United States Patent [19]

Holmes et al.

[11] Patent Number: 5,254,944
[45] Date of Patent: Oct. 19, 1993

[54] INSPECTION PROBE FOR INSPECTING IRREGULARLY-SHAPED TUBULAR MEMBERS FOR ANOMALIES

[75] Inventors: Randall A. Holmes, Delmont; Michael D. Coradi, Wilkinsburg, both of Pa.

[73] Assignee: Westinghouse Electric Corp., Pittsburgh, Pa.

[21] Appl. No.: 868,900

[22] Filed: Apr. 16, 1992

[51] Int. Cl.$^5$ .................... G01N 27/90; G01N 29/04
[52] U.S. Cl. .................... 324/220; 73/623; 73/643; 324/262; 324/238
[58] Field of Search ................ 324/219–221, 324/238, 237, 240, 243, 262; 73/622, 623, 643

[56] References Cited

U.S. PATENT DOCUMENTS

| | | |
|---|---|---|
| 4,276,856 | 7/1981 | Dent et al. |
| 4,471,658 | 9/1984 | Morimoto ............ 324/220 X |
| 4,625,165 | 11/1986 | Rothstein |
| 4,757,258 | 7/1988 | Kelly, Jr. et al. ............ 324/220 |
| 4,772,849 | 9/1988 | Tedder |
| 4,797,613 | 1/1989 | Wentzell |
| 4,851,773 | 7/1989 | Rothstein ............ 324/220 |
| 4,937,524 | 6/1990 | Fasnacht et al. |
| 4,952,875 | 8/1990 | Adams et al. |
| 4,992,735 | 2/1991 | Cullen et al. |
| 5,140,265 | 8/1992 | Sakiyama et al. ............ 324/220 |

Primary Examiner—Gerard R. Strecker
Assistant Examiner—Warren S. Edmonds
Attorney, Agent, or Firm—Walter S. Stevens

[57] ABSTRACT

Inspection probe for inspecting a tubular member for anomalies, the tubular member having an inside surface that may be irregularly-shaped. The inspection probe includes an enclosure sized to be slidably received along the inside surface of the tubular member. The enclosure has a cavity therein and a housing disposed in the cavity. A spring is disposed in the cavity of the enclosure for outwardly biasing the housing toward the inside surface of the tube. A swivel body is pivotably mounted in the housing. The swivel body has a sensor pivotably mounted thereon for sensing anomalies (i.e., flaws and wall thinning) in the tube wall. Connected to the swivel body and to the sensor is a first pivot pin for pivoting the sensor about a first pivot point laying on a first axis extending transversely to the longitudinal axis of the tubular member. In addition, connected to the housing and to the swivel body is a second pivot pin for pivoting the swivel body about a second pivot point laying on a second axis extending parallel to the longitudinal axis of the tubular member. The sensor will continuously engage the inside surface of the tube, even though the inside surface may be irregularly-shaped, because the pivoting action of the housing and the sensor in combination with the biasing action of the spring on the housing will cause the sensor to precisely track the contour of the inside surface of the tubular member.

7 Claims, 5 Drawing Sheets

INSPECTION PROBE FOR INSPECTING IRREGULARLY-SHAPED TUBULAR MEMBERS FOR ANOMALIES

BACKGROUND OF THE INVENTION

This invention generally relates to nondestructive inspection apparatus and more particularly relates to an inspection probe for inspecting a tubular member for anomalies, which tubular member may be a nuclear steam generator heat exchange tube having an irregularly-shaped interior surface.

However, before describing the subject matter of the present invention, it is instructive first to briefly discuss the structure and operation of a typical nuclear steam generator, which contains a plurality of U-shaped heat exchange tubes. In this regard, a nuclear steam generator is a device for generating steam as heat is transferred from a radioactive primary fluid (i.e., water) to a non-radioactive secondary fluid (i.e., water) across a heat conductor boundary separating the primary fluid from the secondary fluid. The primary fluid flows through the tubes, which function as the heat conductor boundary, as the secondary fluid surrounds the tubes. Each tube is supported along its length by a plurality of tube support plates having holes therethrough for receiving each tube. Moreover, the ends of each U-shaped tube are supported by a tube sheet having apertures therethrough for receiving each tube. Although each tube matingly passes through holes and apertures in the support plates and tube sheet, respectively, a relatively small annular gap may nonetheless exist at the interface of the tube and support plate and at the interface of the tube and tube sheet.

As stated hereinabove, the primary fluid flowing in the tubes is radioactive; hence, for safety reasons the steam generator is designed such that the radioactive primary fluid does not radioactively contaminate the non-radioactive secondary fluid by co-mingling with the secondary fluid. It is therefore desirable that the tubes remain leak-tight during operation of the steam generator so that the radioactive primary fluid remains everywhere separated from the non-radioactive secondary fluid to avoid co-mingling the primary fluid with the secondary fluid.

Occasionally, however, the steam generator tubes may develop surface and volume anomalies (i.e., flaws and tube wall thinning) and thus may not remain leak-tight. Such anomalies may be caused by vibration and by intragranular cracking due to stress and corrosion during operation. If through-wall anomalies are present, the primary fluid may co-mingle with the secondary fluid. Such through-wall anomalies typically occur, if at all, in a tube portion adjacent the gap due to the flow-induced tube vibration and intragranular stress corrosion cracking at that location. That is, the flow-induced vibration of the tube against the support plate or against the tube sheet may lead to wearing of the tube wall. Moreover, potentially corrosive contaminants, which usually appear in the form of sludge deposits comprising iron oxides, copper compounds, and other metals, may settle out of the secondary fluid onto the tube sheet and support plates and then migrate into the gap to constrict, stress and corrode the tube and thus lead to the stress corrosion cracking previously mentioned. Therefore, it is desirable to inspect the tubes for anomalies that are indicative of incipient flaws or through-wall cracks caused by vibration and/or stress corrosion cracking. Such an inspection is usually performed by engaging a suitable radially rotating sensor with the inside surface of the tube. Once such incipient flaws or through-wall cracks are discovered during the inspection process, the tube is either sleeved at the location of the anomaly or plugged, in a manner well known in the art, to prevent the primary fluid from co-mingling with the secondary fluid.

However, the steam generator tube being inspected may have an interior surface that is out-of-round or slightly irregularly-shaped, particularly at the site of the anomaly. The operator of the inspection probe therefore may encounter difficulty inspecting such a tube that is not perfectly round. That is, the irregular shape of the inside surface of the tube may cause the sensor previously mentioned to disengage or lose contact with a portion of the inside surface of the tube as the sensor rotates within the tube. This result is undesirable because each time the sensor loses contact with the inside surface of the tube, the inspection signal generated by the sensor is interrupted. This necessarily causes the operator of the inspection device to reinspect the tube in order to achieve an acceptable inspection signal. Such reinspection increases the time for completing the inspection process. Of course, increasing the time necessary for inspecting the tube increases inspection costs. It is therefore desirable to perform the inspection of the tube using an inspecting device that will allow the sensor to remain in continuous contact with the inside surface of the tube, even though the inside surface of the tube is irregularly-shaped.

Inspection devices for inspecting tubing are known. One such device is disclosed in U.S. Pat. No. 4,937,524 entitled "Rotating Eddy Current Roller Head For Inspecting Tubing" issued Jun. 26, 1991 to Floyd A. Fasnacht et al. This patent discloses a rotating eddy current roller head for inspecting a tube. The device includes a main body portion having a set of wheels attached thereto which center the main body portion in the tube. A roller housing, which is slidably mounted on the main body portion for radial movement relative thereto, is caused to track the surface of the tube by action of opposing magnets mounted in the main body portion and roller housing. An eddy current coil is mounted in a coil holder, which is pivotally mounted at the exterior end of the roller housing, and a spring is mounted in the roller housing to bias the coil holder against the surface of the tube for maintaining the eddy current coil at a constant distance from the surface of the tube during the inspection process. Although this patent discloses an eddy current coil mounted in a coil holder which is pivotally mounted at the end of a roller housing and a spring mounted in the roller housing to bias the coil holder against the surface of the tube, this patent does not appear to disclose an inspection probe for suitably inspecting tubular members that are out-of-round, as described and claimed herein.

Another eddy current inspection device is disclosed in U.S. Pat. No. 4,625,165 entitled "Tube Inspection Probe With Rotating Eddy Current Coil" issued Nov. 25, 1986 to Samuel Rothstein. This patent discloses an electro-mechanical eddy current probe having a rotatable sensing head for sensing the wall thickness of and locating local defects in a tube or conduit through which it is passed. The rotatable head of this device includes a radially movable, outward projecting sensing member which is spring-biased into engagement with the interior surface of the tube and which carries an eddy current coil electrically monitored by the probe. Although this patent discloses a radially movable, outward projecting sensing member which is spring-biased into engagement with the interior surface of the tube, this patent does not appear to disclose an inspection probe for suitably inspecting tubular members that are out-of-round, as described and claimed herein.

Therefore, what is needed is an inspection probe for inspecting a tubular member for anomalies, wherein the tubular member has an out-of-round interior surface.

SUMMARY OF THE INVENTION

Disclosed herein is an inspection probe for inspecting a tubular member for anomalies, which tubular member may have an inside surface that is out-of-round or irregularly-shaped. The inspection probe includes an enclosure sized to be slidably received along the inside surface of the tubular member. The enclosure, which has a cavity therein, has a housing disposed in the cavity. The housing has a hollow portion for receiving a swivel body mounted in the hollow portion of the housing. The swivel body has a recess therein and a sensor mounted in the recess for sensing anomalies (i.e., flaws and wall thinning) in the tubular member. Moreover, a spring is disposed in the cavity of the enclosure for outwardly biasing the housing toward the inside surface of the tubular member. Connected to the swivel body and to the sensor is a first pivot pin for pivoting the sensor about a first pivot point laying on a first axis extending transversely to the longitudinal axis of the tubular member. In addition, connected to the housing and to the swivel body is a second pivot pin for pivoting the swivel body about a second pivot point laying on a second axis extending parallel to the longitudinal axis of the tubular member. The sensor will intimately engage the inside surface of the tubular member, even though the inside surface may be irregularly-shaped, because the pivoting action of the housing and the sensor in combination with the biasing action of the spring on the housing will cause the sensor to precisely track or follow the inside surface of the tubular member.

An object of the present invention is to provide an inspection probe for inspecting a tubular member for anomalies, which tubular member may be a nuclear steam generator heat exchange tube having an irregularly-shaped interior surface.

A feature of the present invention is the provision of dual pivoting means for pivoting the sensor in two directions as it is simultaneously outwardly biased in order to continuously engage the sensor with the inside surface of the tube even though the inside surface may be irregularly-shaped.

An advantage of the present invention is that the sensor remains continuously engaged with the inside surface of the tube to avoid reinspecting the tube so that the total time for performing the inspection of a tubular member having an irregularly-shaped inside surface is reduced.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings wherein:

DESCRIPTION OF THE PREFERRED EMBODIMENT

Nuclear steam generators comprise a plurality of heat exchange tubes disposed therein for transferring heat from the radioactive primary fluid flowing through the tubes to the nonradioactive secondary fluid surrounding the tubes. For safety reasons, it is important that the primary fluid remains everywhere separated from the secondary fluid so that the primary fluid does not comingle with the secondary fluid to radioactively contaminate the secondary fluid. Therefore, the tubes are nondestructively inspected by a suitable sensor that engages the interior surface of the tube to ascertain if the tube has anomalies indicative of incipient flaws or cracks that could ultimately lead to the primary fluid commingling with the secondary fluid. However, the interior surface of the tube may be out-of-round thereby causing the sensor to disengage that portion of the interior surface being inspected. This would result in the sensor's inspection signal being interrupted. It is hence desirable to inspect the tube using an inspection apparatus that remains continuously engaged with the interior surface of the tube so that the inspection signal is not interrupted, even though the interior surface may be irregularly-shaped. Therefore, disclosed herein is the preferred embodiment of the present invention, which is an inspection probe for inspecting a heat exchange tube for anomalies, wherein the tube has an out-of-round or irregularly-shaped interior surface.

However, before disclosing the subject matter of the present invention, it is instructive first to briefly describe the structure and operation of a typical nuclear steam generator, which contains the heat exchange tubes.

Figure 1:
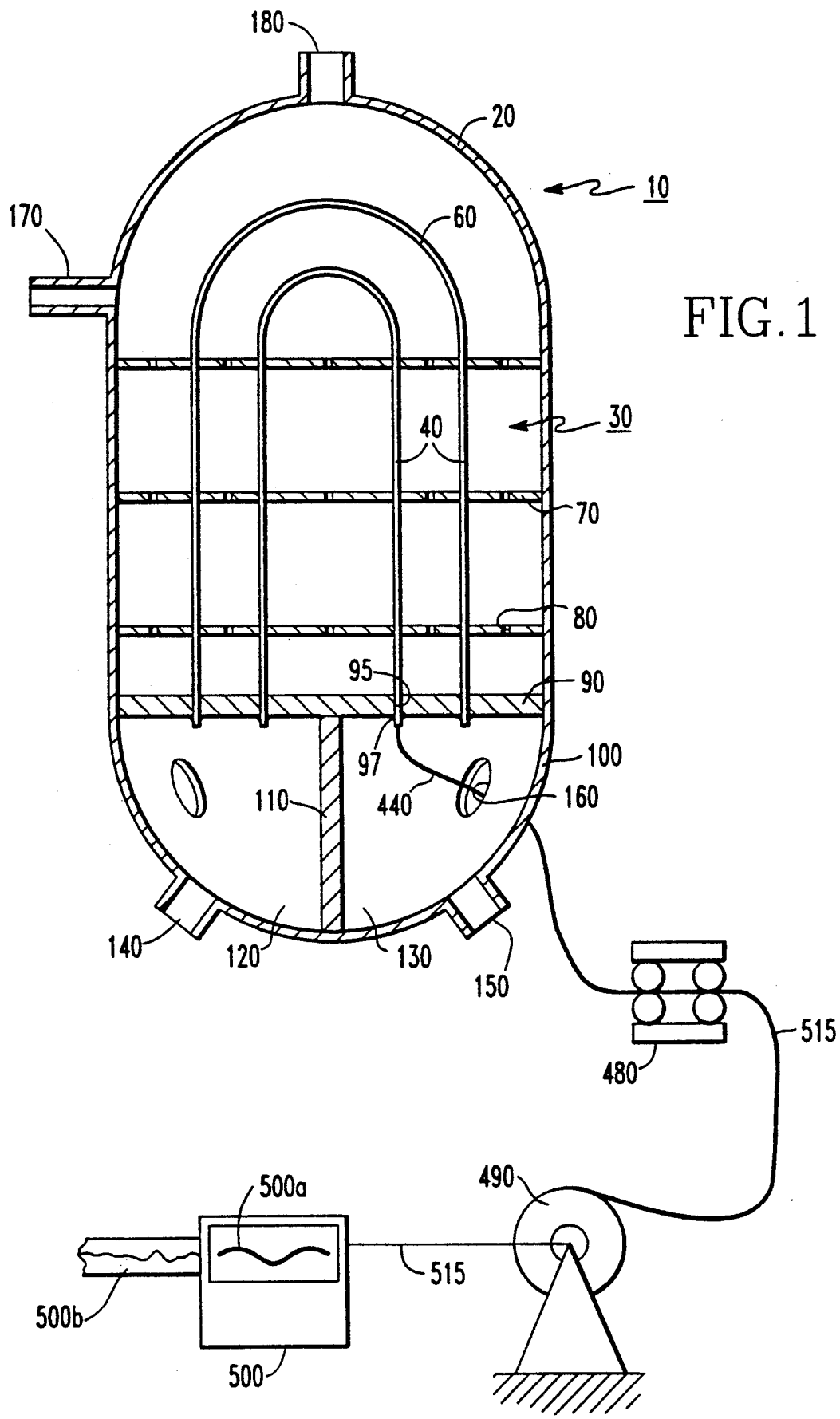
FIG. 1 illustrates in partial vertical section, a typical nuclear steam generator with parts removed for clarity, the steam generator having a plurality of heat exchange tubes disposed therein.
Figure 2:
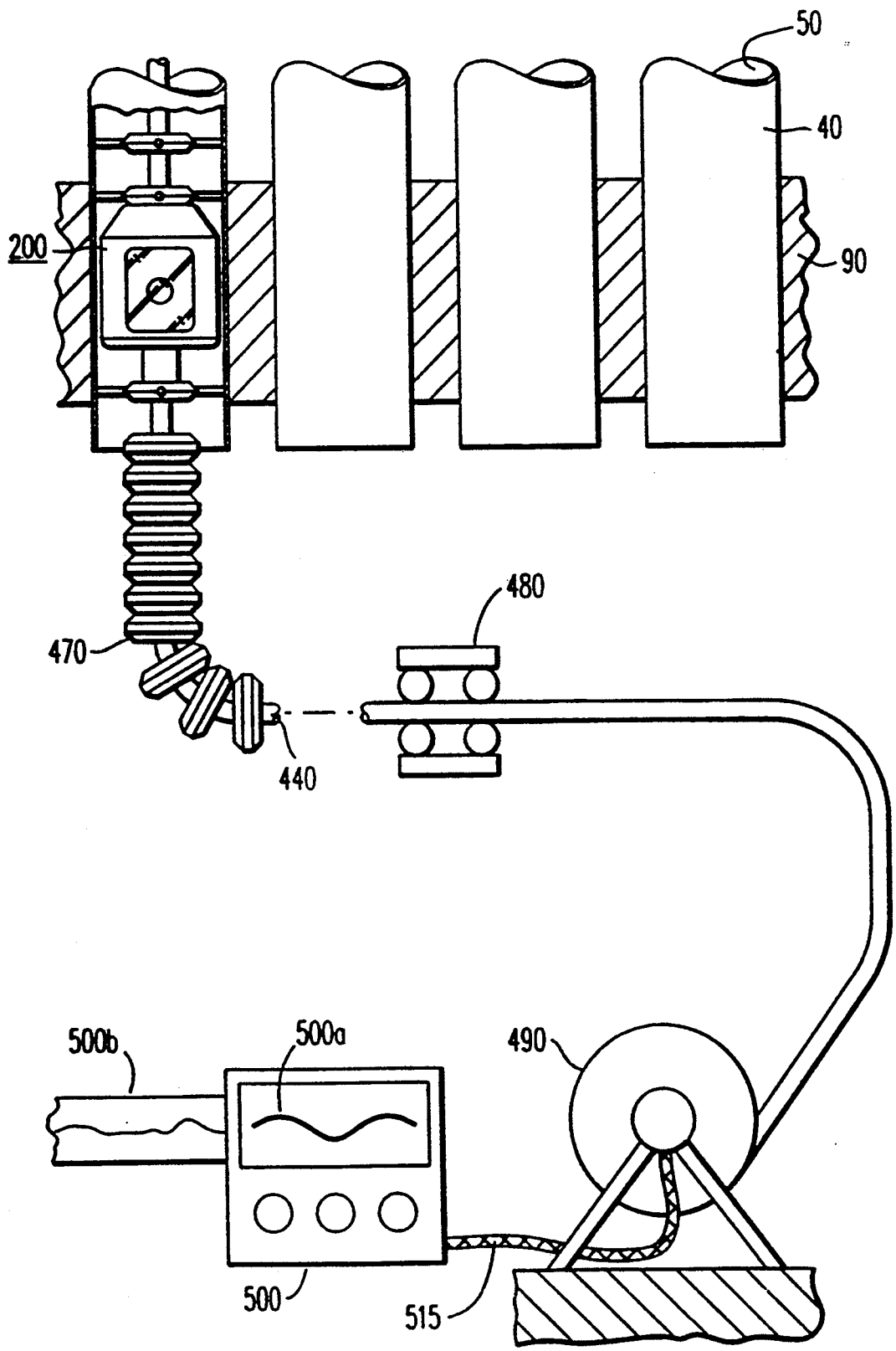
FIG. 2 illustrates the inspection probe of the invention positioned to be inserted into a preselected one of the tubes.

Therefore, referring to FIG. 1, there is shown a typical nuclear steam generator, generally referred to as 10, for generating steam. Steam generator 10 comprises a shell 20 having a vertically-oriented tube bundle 30 disposed therein. Bundle 30 comprises a plurality of inverted U-shaped tubes 40 (only two of which are shown), which may be mill annealed, thermally treated "INCONEL" alloy for resisting stress corrosion cracking. Such an "INCONEL" alloy is composed substantially of nickel, chromium, and iron and a trace amount of cobalt. Each of tubes 40 has an inside surface 50 (see FIG. 2) defining a longitudinal axis through tube 40 and each tube 40 also has a U-bend region 60 defined by the U-shape of tube 40. As shown in FIG. 1, disposed along the axial length of tube bundle 30 are a plurality of spaced-apart horizontal, circular tube support plates 70 having holes 80 therethrough for receiving each tube 40, for laterally supporting tubes 40 and for reducing flow-induced vibration in tubes 40. Disposed below the lower-most of support plates 70 is a horizontal, circular tube sheet 90 having apertures 95 therethrough for receiving the ends of tubes 40. The ends of each tube 40 are attached, such as by weldments 97, to tube sheet 90 for supporting each tube 40. Tube sheet 90 is sealingly attached around its circumferential edge to a hemispherical channel head 100 belonging to shell 20. Disposed in channel head 100 is a vertical, semi-circular divider plate 110 sealingly attached to channel head 100 and to tube sheet 90. Divider plate 110 divides channel head 100 into an inlet plenum chamber 120 and an outlet plenum chamber 130. Moreover, disposed on shell 20 are an inlet nozzle 140 and an outlet nozzle 150 in fluid communication with inlet plenum chamber 120 and outlet plenum chamber 130, respectively. A plurality of manway holes 160 (only two of which are shown) are formed in shell 20 below tube sheet 90 for providing access to inlet plenum chamber 120 and outlet plenum chamber 130, so that maintenance (e.g., tube inspection) may be performed in steam generator 10. Disposed on shell 20 above tube sheet 90 is a feedwater nozzle 170 for allowing entry of non-radioactive secondary fluid (e.g., water) into shell 20. In addition, a steam line nozzle 180 is disposed on shell 20 at the top portion thereof for exit of steam from steam generator 10.

During operation of steam generator 10, radioactive primary fluid (i.e., water) enters inlet plenum chamber 120 through inlet nozzle 140 and flows through tubes 40 to outlet plenum chamber 130 where the primary fluid exits shell 20 through outlet nozzle 150. As the primary fluid enters inlet plenum chamber 120, non-radioactive secondary fluid simultaneously enters shell 20 through feedwater nozzle 170. The secondary fluid vaporizes into steam which travels upwardly through steam line nozzle 180. The steam traveling through steam line nozzle 180 is piped to a turbine-generator (not shown) for generating electricity in a manner well known in the art of electrical power generation. Such a nuclear steam generator is more fully disclosed in U.S. Pat. No. 4,276,856 entitled "Steam Generator Sludge Lancing Method" issued Jul. 7, 1981 to Thomas H. Dent et al. and assigned to the assignee of the present invention, the disclosure of which is hereby incorporated by reference.

The interface between aperture 95 and the outer surface of tube 40 (or the interface between hole 80 and the outer surface of tube 40) often obtains a relatively small annular gap 190 (see FIG. 3) surrounding tube 40. Potentially corrosive sludges (not shown), that settle-out from the secondary fluid, can accumulate on the top surface of tube sheet 90 (or support plate 70) and flow downwardly into gap 190 during operation of steam generator 10. Moreover, efforts to close gap 190 by expanding tube 40 at the location of aperture 95 (or hole 80) may not completely eliminate gap 190. The exposure of the exterior surface of tube 40 to the sludge and heat, in combination with mechanical stresses induced in tube 40 particularly during tube expansion to eliminate gap 190, may cause tube 40 to corrode and crack due to intragranular stress corrosion. Such stress corrosion cracking, if severe enough, may lead to the primary fluid commingling with the secondary fluid, which is an undesirable result. Therefore, tubes 40 are periodically inspected along their lengths for anomalies that are indicative of incipient flaws and cracks caused by vibration and stress corrosion cracking.

Therefore, referring now to FIGS. 2, 3, 4, and 5, there is shown an inspection probe, generally referred to as 200, for inspecting tube 40 for anomalies. Inspection probe 200 comprises a generally barrel-shaped enclosure 210 having a generally rounded distal end nose portion 220 and a proximal end rear portion 230. Distal end portion 220 is rounded for ease of insertion into tube 40. The term "proximal end portion" is defined herein to mean that end portion that is nearer the lowest point of channel head 100 and the term "distal end portion" is defined to mean that end portion that is farther away from the lowest point of channel head 100 when probe 200 is disposed in channel head 100. For reasons disclosed hereinbelow, enclosure 210 is preferably made of a non-magnetic material, such as "DELRIN" or the like, available from E. I. DuPoint De Nemours and Company located in Wilmington, Del. Enclosure 210 is non-magnetic so that enclosure 210 will not interfere with electromagnetic inspection signals emitted and received by an inspection sensor. Enclosure 210, which is sized to be inserted into tube 40, has a generally cylindrical cavity 240 therein defining a generally circular opening or open end 250 facing inside surface 50 of tube 40 and also defining a rear wall 260 therein opposite open end 250. Formed in rear wall 260 may be a blind bore 270 for reasons disclosed hereinbelow. Integrally attached to proximal end portion 230 of enclosure 210 is a generally cylindrical enclosure extension 280 outwardly extending posteriorly of proximal end portion 230 for reasons disclosed hereinbelow. Axially extending through enclosure extension 280, through proximal end portion 230 and in communication with cavity 240 is a bore 290 for reasons disclosed hereinbelow. Moreover, formed longitudinally in enclosure extension 280 is a blind bore 300 for reasons more fully disclosed hereinbelow. In addition, axially formed in distal end nose portion 220 is a blind bore 310 for reasons disclosed hereinbelow.

Figure 5:
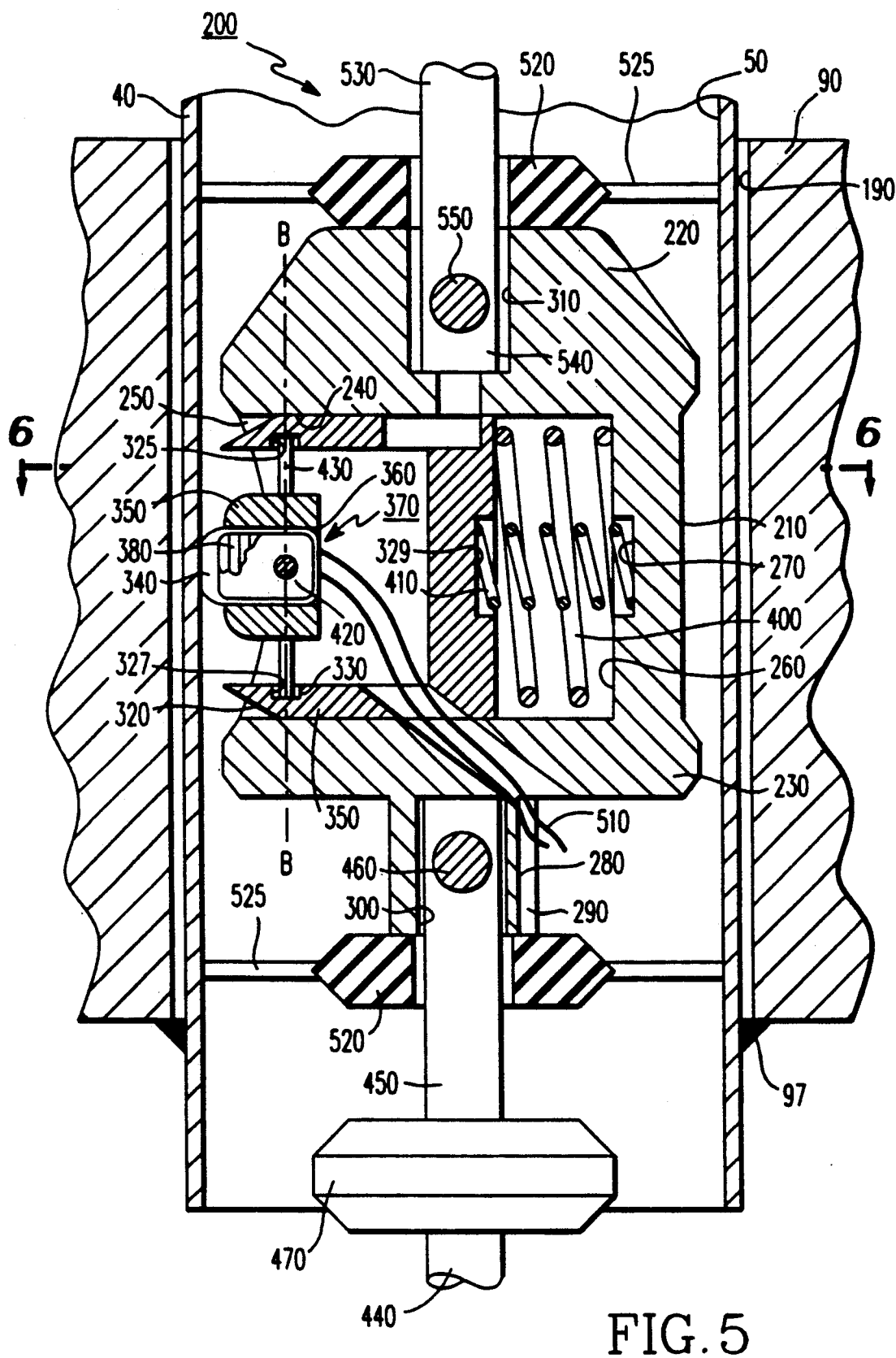
FIG. 5 is a view of the inspection probe disposed in the tube taken along section line V—V of FIG. 4.

As best seen in FIG. 5, slidably received through open end 250 of enclosure 210 is a generally cylindrical housing 320, which may be formed of "DELRIN", having a hollow portion 330 therein defining an open end 340 facing inside surface 50 of tube 40. Housing 320 also has coaxially disposed holes 325 and 327 formed therein and may have a blind hole 329 facing blind bore 270 of enclosure 210 for reasons disclosed hereinbelow. Extending from hollow portion 330 to bore 290 is a bore 350 for reasons disclosed presently. Pivotally mounted in open end 340 of housing 320 is a generally cylindrical swivel body 350 having a recess 360 therein facing inside surface 50 of tube 40. Pivotably mounted in recess 360 is a sensor, generally referred to as 370, for sensing anomalies in tube 40. Sensor 370 comprises a sensor coil 380, which is preferably an eddy current sensor coil for generating electromagnetic eddy currents in tube 40 and for sensing the electromagnetic currents generated in tube 40. Alternatively, sensor coil 380 may be an ultrasonic transducer for generating relatively high frequency sound waves in tube 40 and for sensing the sound waves reflected by tube 40. In either case, coil 380 may be preferably surrounded by coil holder 390 substantially formed of a transparent non-magnetic material having a relatively low coefficient of friction, such as the acrylic material "PLEXIGLAS", or the like. Coil holder 390 is preferably non-magnetic so that coil holder 390 will not interfere with the electromagnetic sensing signals emitted and received by coil 380. Coil holder 390 is preferably transparent for visually inspecting coil 380 for damage. In addition, coil holder 390 has a low-coefficient of friction so that it will easily rotatably slide along inside surface 50 of tube 40. Coil holder 390 may be removably secured in recess 360 by any suitable means, such as by a press fit.

Referring yet again to FIG. 5, biasing means, such as a resilient coil spring 400 is disposed in cavity 260 of housing 210 and interposed between housing 210 and enclosure 320 for slidably outwardly biasing or urging housing 210 toward inside surface 50 of tube 40. Spring 400 may be formed of a non-magnetic spring steel material so that the material comprising spring 400 will not interfere with the electromagnetic signals generated and received by coil 380. Moreover, if desired, extending from blind bore 270 of enclosure 210 to blind bore 329 of housing 320 may be another spring 410, likewise formed of non-magnetic spring steel, for slidably outwardly biasing or urging housing 210 toward inside surface 50 of tube 40. Use of spring 410 in combination with spring 400 will increase the springing action of housing 320 so as to increase the outwardly directed force acting against housing 320. Increasing the force acting against housing 320 will increase the likelihood that sensor 370 will remain continuously engaged with inside surface 50 as sensor 370 radially axially inspects tube 40.

Figure 6:
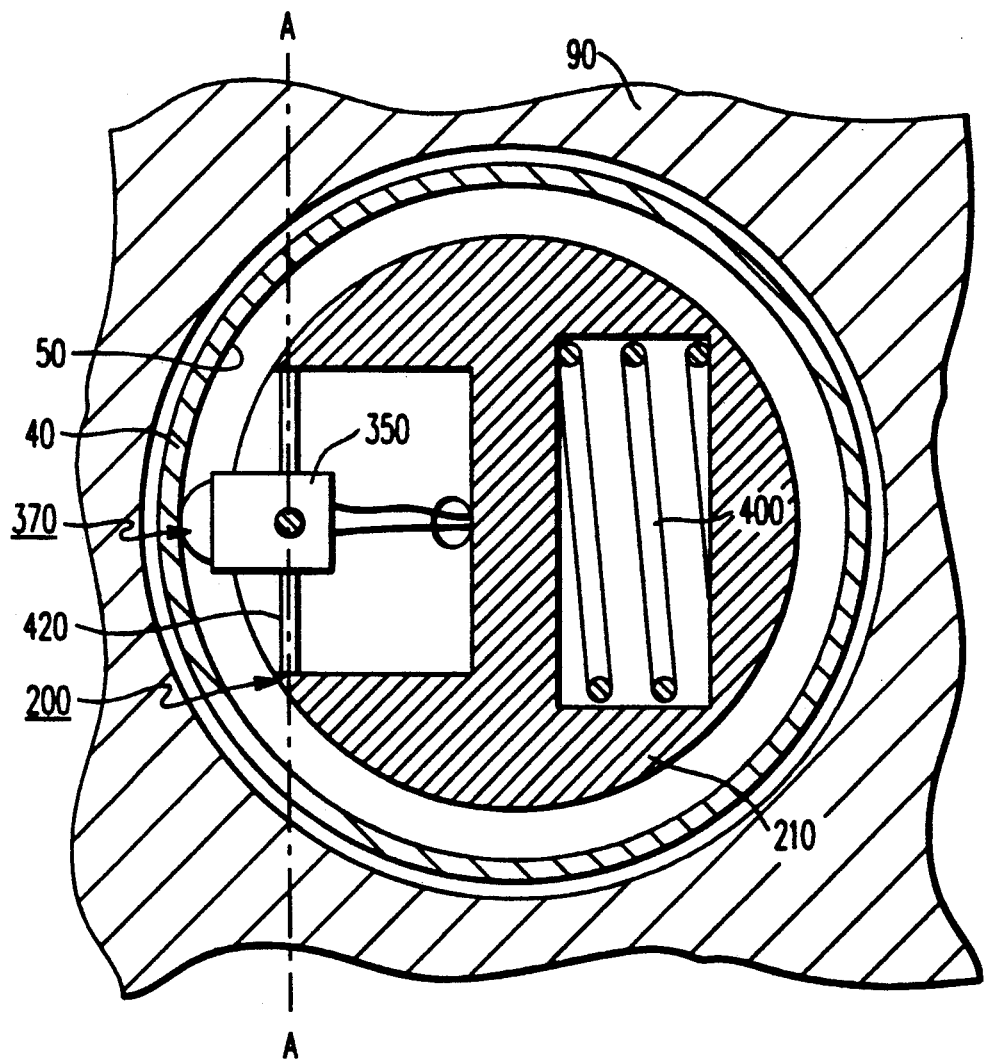
FIG. 6 is a view of the inspection probe disposed in the tube taken along section line VI—VI of FIG. 5.

As best seen in FIGS. 5 and 6, first pivot means, such as a generally cylindrical first axle or first pivot pin 420, has a first end portion rotatably connected to swivel body 350 and a second end portion attached to sensor 370 for pivoting sensor 370 about a first pivot point laying on a first axis A—A (see FIG. 6) extending transversely to the longitudinal axis defined by tube 40. In this regard, it will be appreciated that sensor 370 will pivot in an arc as illustrated by the double-headed arrow of FIG. 5. Moreover, second pivot means, such as a generally cylindrical second axle or second pivot pin 430, has a first end portion rotatably connected to housing 210 and a second end portion attached to swivel body 350 for pivoting swivel body 350 about a second pivot point laying on a second axis B—B (see FIG. 5) extending parallel to the longitudinal axis of tube 40. Thus, second pivot pin 430 is disposed transversely with respect to first pivot pin 420. In this regard, it will appreciated that swivel body 350 will pivot in an arc as illustrated by the double-headed arrow of FIG. 6. It also will be appreciated from the disclosure hereinabove that sensor 370 will intimately engage inside surface 50 of tube 40 to precisely track inside surface 50 as housing 320 is outwardly biased by spring 400 and as sensor 370 pivots about the first pivot point and as swivel body 350 pivots about the second pivot point. In other words, housing 210 and sensor 370 together comprise a double gimbal for enabling sensor 370 to be freely pivotable in order to precisely track the irregular shape of inside surface 50 of tube 40.

Returning now to FIGS. 1, 2, 3, 4, and 5, an elongate flexible probe carrier or flexible cable 440 is removably connected to enclosure extension 280 for carrying enclosure 320 along inside surface 50 of tube 40. For the purpose of removably connecting cable 440 to enclosure extension 280, cable 440 has a first end portion 450 received in blind bore 300 and removably connected therein, such as by screw fastener 460. It is important that cable 440 be flexible so that it can bend to flexibly move through the U-bend region 60 of tube 40. Axially spaced along and surrounding a substantial portion of cable 440 are a multiplicity of beads 470 for enabling cable 440 to be relatively stiff while simultaneously remaining flexible so that cable 440 can be easily moved within tube 40 without binding (i.e., folding back on itself). The flexibility of cable 440 is particularly advantageous for allowing cable 440 to bend along the relatively narrow radius the inner-most tubes of tube bundle 30. Engaging cable 440 is a probe pusher/puller mechanism 480 for pushing and pulling cable 440 so that enclosure 210 can be pushed and pulled axially along inside surface 50 of tube 40. In this regard, cable 440 is pushed by pusher/puller mechanism 480 for advancing enclosure 210 within tube 40 and pulled by pusher/puller mechanism 480 for retracting enclosure 210 from tube 40. Moreover, pusher/puller mechanism 480 is capable of also rotating cable 440 for radially rotating enclosure 210 so that sensor 370 inspects tube 40 in a helical scanning pattern to suitably inspect tube 40 for anomalies. Cable 440 is fed to pusher/puller mechanism 480 from a take-up reel 490 about which cable 440 is wound. An activation-display means, such as a strip recorder or computer 500, is also provided for activating sensor 370 and for displaying the anomalies sensed by sensor 370. The anomalies may be displayed by computer 500 in the form of visible lines on an oscilloscope-like monitor 500a and/or in the form of a strip chart 500b. In this regard, computer 500 is electrically connected to sensor 370 by electrically conducting wires 510, which wires 510 may extend from sensor 370, through bores 350 and 290, along cable 440 and to take-up reel 490 and there electrically connected to computer 500, such as by electrically-conducting wire cable 515.

Figure 4:
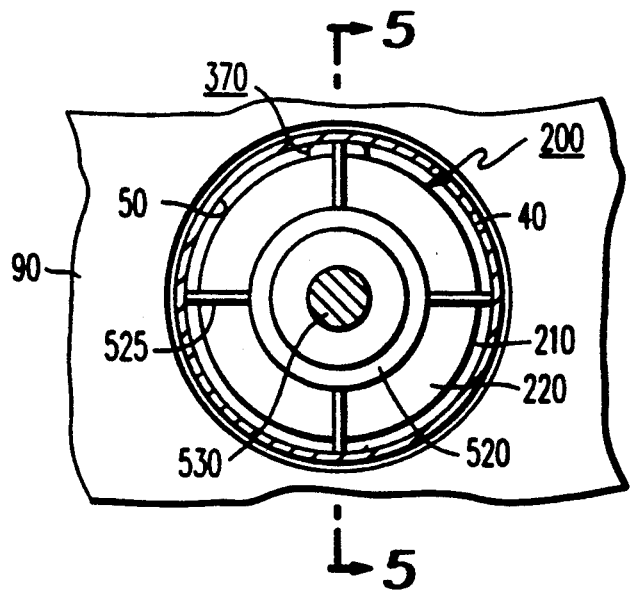
FIG. 4 is a view of the inspection probe disposed in the tube taken along section line IV—IV of FIG. 3.
Figure 3:
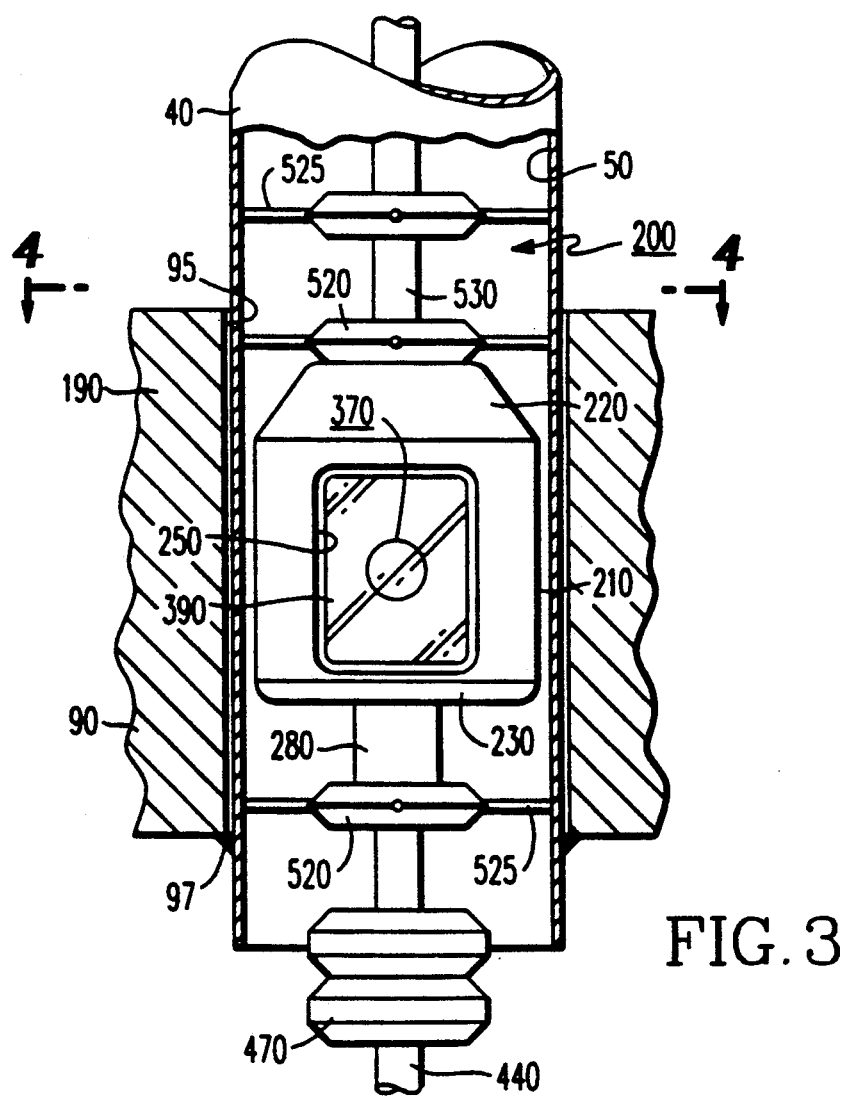
FIG. 3 shows in partial vertical section, the inspection probe disposed in the tube.

Moreover, as best illustrated in FIGS. 3, 4, and 5, centering means, such as a plurality of pin-wheels 520, are attached to cable 440 near enclosure 210 for centering enclosure 210 coaxially with respect to the longitudinal axis of tube 40. Each pin-wheel 520 comprises a plurality of radially outwardly extending wire spokes 525 adapted to engage inside surface 50 of tube 40. Centering enclosure 210 within tube 40 is important to assist in maintaining enclosure 210 at a constant distance from inside surface 50 of tube 40 for generating reliable sensing signals. To ensure that enclosure 210 is centered within tube 40, an additional relatively stiff but flexible cable 530 having an end portion 540 received in blind bore 310, may be provided, which cable 530 has a plurality of pin-wheels attached axially therealong. End portion 540 may be secured in blind bore 310 by any suitable means, such as by a screw fastener 550.

OPERATION

During operation, steam generator 10 is first shut-down and drained of primary and secondary fluids in a manner well known in the art. Manway holes 160 are uncovered and probe 200 is then inserted through manway 160 and into either inlet plenum 120 or outlet plenum 130 to inspect a preselected tube 40 for anomalies. Cable 530 and enclosure 210 are positioned coaxially beneath the tube 40 to be inspected and inserted through the mouth of tube 40 using any suitable means, such as a Remotely Operated Service Arm (ROSA) available from Westinghouse Electric Corporation located in Pittsburgh, Pa. Pusher/puller mechanism 480 is operated to drive cable 440 through tube 40 such that sensor 370 moves along inside surface 50 of tube 40 in a helical scanning path for suitably inspecting tube 40. Activation-display means 500 is operated to activate sensor 370 for sensing anomalies in tube 40 and for displaying the anomalies sensed by sensor 370.

As stated hereinabove, inside surface 50 may be slightly out-of-round or irregularly-shaped. Therefore, as sensor 370 rotatably and axially engages inside surface 50, it will track inside surface 50, in the manner disclose immediately hereinbelow, so that the signal from sensor 370 is not interrupted. That is, as sensor 370 tracks inside surface 50, it will pivot about the first pivot point and the second pivot point so that sensor 370 will remain continuously intimately engaged with and follow the contour of inside surface 50 even though inside surface 50 is irregularly-shaped. Moreover, as sensor 370 tracks inside surface 50, the outwardly directed force of spring 400 will outwardly bias or urge housing 210 and thus sensor 370 into further intimate engagement with inside surface 50 of tube 40. If sensor 370 is an eddy current sensor coil, it will induce electromagnetic eddy currents in tube 40 and will also sense the electromagnetic currents induced in tube 40. Alternatively, if sensor 370 is an ultrasonic sensor coil 380, it will emanate relatively high frequency sound waves in tube 40 and will sense the sound waves of altered frequency reflected by tube 40. For this purpose, activation-display means 500 is operated to activate sensor 370 as sensor radially axially moves along inside surface 50 of tube 40 by action of pusher/puller mechanism 480. If an anomaly is discovered in tube 40, the tube 40 having the anomaly is either plugged or sleeved in a manner well known in the art.

Although the invention is fully illustrated and described herein, it is not intended that the invention as illustrated and described be limited to the details shown, because various modifications may be obtained with respect to the invention without departing from the spirit of the invention or the scope of equivalents thereof. For example, although the preferred embodiment of the invention is disclosed with particular reference to nondestructive examination of out-of-round nuclear steam generator tubes, the invention is suitable for use wherever nondestructive examination of an out-of-round tubular member is desired.

Therefore, what is provided is an inspection probe for inspecting a tubular member for anomalies, which tubular member may be a nuclear steam generator heat exchange tube having an irregularly-shaped interior surface.

What is claimed is:

1. In a heat exchanger having a plurality of heat exchange tubes disposed therein, each of the tubes having a U-bend region, an inspection probe for inspecting a predetermined one of the tubes for anomalies, the tubes having an irregularly-shaped inside surface and defining a longitudinal axis therethrough, comprising;
   (a) a generally barrel-shaped enclosure sized to be inserted into the tube, said enclosure having a generally cylindrical cavity therein having a generally circular open end facing the inside surface of the tube;
   (b) a generally cylindrical housing slidably received through the open end of the cavity of said enclosure, said housing having a hollow portion therein having an open end facing the inside surface of the tube;
   (c) a generally cylindrical swivel body pivotably mounted in the open end of the hollow portion of said housing, said swivel body having a recess therein facing the inside surface of the tube;
   (d) a sensor pivotably mounted in the recess of said swivel body for sensing anomalies in the tube;
   (e) a coil spring disposed in the cavity of said housing and interposed between said housing and said enclosure for slidably outwardly biasing said housing toward the inside surface of the tube;
   (f) a generally cylindrical first pivot pin having a first end portion rotatably connected to said swivel body and having a second end portion attached to said sensor for pivoting said sensor about a first pivot point laying on a first axis extending transversely to the longitudinal axis defined by the tube; and
   (g) a generally cylindrical second pivot pin having a first end portion rotatably connected to said housing and a second end portion attached to said swivel body and disposed transversely with respect to said first pivot pin for pivoting said swivel body about a second pivot point laying on a second axis extending parallel to the longitudinal axis of the tube, whereby said sensor intimately engages the inside surface of the tube to precisely track the inside surface as said housing is outwardly biased by said spring, as said sensor pivots about the first pivot point, and as said swivel body pivots about the second pivot point.

2. The inspection probe of claim 1, further comprising an elongate flexible cable connected to said enclosure for rotatably carrying said enclosure along the inside surface of the tube, said cable being flexible for flexibly moving through the U-bend region of the tube.

3. The inspection probe of claim 2, further comprising a pusher/puller mechanism engaging said cable for rotatably pushing and pulling said cable along the inside surface of the tube so that said sensor inspects the tube along a helical path.

4. The inspection probe of claim 3, further comprising activation-display means electrically connected to said sensor for activating said sensor and for displaying the anomalies sensed by said sensor.

5. The inspection probe of claim 4, further comprising centering means for centering said enclosure in the tube coaxially with respect to the longitudinal axis of the tube.

6. The inspection probe of claim 1, wherein said sensor is an eddy current coil for generating electromagnetic eddy currents in the tube and for sensing the electromagnetic currents generated in the tube.

7. The inspection probe of claim 1, wherein said sensor is an ultrasonic transducer for generating high frequency sound waves in the tube and for sensing the sound waves reflected by the tube.

* * * * *